United States Patent [19]

Thompson et al.

[11] Patent Number: 4,660,462
[45] Date of Patent: Apr. 28, 1987

[54] VENTILATION SYSTEM AND FILTER

[75] Inventors: James E. Thompson, Cedar Falls; Nicholas S. Novick, Denver, both of Iowa

[73] Assignee: Deere & Company, Moline, Ill.

[21] Appl. No.: 764,362

[22] Filed: Aug. 12, 1985

[51] Int. Cl.4 .............................................. B60H 3/06
[52] U.S. Cl. ...................................... 98/2.11; 55/473; 55/480; 55/481; 55/498; 55/506
[58] Field of Search ................. 55/473, 480, 481, 493, 55/498, 506, 510, 521; 98/2.11

[56] References Cited

U.S. PATENT DOCUMENTS

| | | | |
|---|---|---|---|
| 2,954,096 | 9/1960 | McMullen | 55/480 X |
| 3,319,404 | 5/1967 | Lowther | 55/481 X |
| 3,657,992 | 4/1972 | Minnick, Jr. | 98/2.11 |
| 4,233,043 | 11/1980 | Catterson | 55/473 X |

FOREIGN PATENT DOCUMENTS 155109  9/1982  Japan ..................................... 98/2.11

Primary Examiner—Harold Joyce

[57] ABSTRACT

An air distribution system for a vehicle cab is disclosed herein. Fresh air is drawn into the system, filtered and transferred to the interior of the vehicle cab. The system uses a blower for transferring air into the cab with all fresh air passing first through a fresh air filter. The fresh air filter has air flow from a hollow interior out through air permeable sides. This air flow traps particulates within the interior of the filter which is then easily removed from an air filter chamber without emptying dirt into the chamber or on the operator. Furthermore during operation, accumulated dust and dirt is kept within the filter and does not drop off on or around the cab. This system may be used for simple ventilation or may be combined with other air conditioning and air recirculation means thereby providing a total vehicle ventilation system.

11 Claims, 3 Drawing Figures

VENTILATION SYSTEM AND FILTER

BACKGROUND OF THE INVENTION

1. Field of the Invention

This invention relates to an air distribution system and, in particular, to an air distribution system for a vehicle cab.

2. Description of the Prior Art

Vehicles, such as agricultural tractors, typically employ means for protecting the vehicle operator from dust, noise and air temperature extremes. Ventilation systems to which this invention will apply, take fresh air in from the outside and deliver it, treated or untreated, to the interior of the cab.

In collecting air from the outside, large quantities of dust are also taken and must be removed before the air is transferred into the cab. The quantity of air will vary depending on the type of ventilation system in use. In some ventilation systems such as the constant pressurization system disclosed in U.S. Pat. No. 4,344,356 to Casterton, fresh air is used to pressurize the interior of the cab and keep dust from entering through other cracks and crevices within the cab body. Other ventilation systems take in large quantities of fresh air which are passed into the cab and vented out with no additional pressurization of the cab. In either case, the dust from the fresh air is typically collected by a filter.

Ordinary fresh air filters for vehicle cabs collect dust or airborne particulate material on the upstream surface of a filter face disposed between the air inlet and the vehicle cab outlet. These filters come in many shapes and configurations. In the past, fresh air filters were located in a chamber from which the filter could be extracted and cleaned. However, vibration of the vehicle would cause dust to fall off the face of the filter and collect in the chamber. The collection of dust in the chamber and the tendency of particles to fall off the filter made cleaning of the filter element an inconvenient and messy job. Such problems were exacerbated where the filter system was located in the roof of a vehicle cab along with the rest of the ventilation system. In such systems, dust and dirt would often fall on the operator when opening the chamber to take out the filter and perform cleaning.

In order to overcome some of the previously mentioned difficulties and also to reduce the required frequency of cleaning, filter elements have been located on the exterior of vehicle cabs. A filter of this type mounted on the rearward roof portion of a vehicle cab is shown in U.S. Pat. No. 3,868,896 issued to Dahl et al. The collection face of the filter in Dahl faces downward and is uncovered allowing particles to drop off along the back window of the vehicle cab. Another system along the lines of Dahl is disclosed in U.S. Pat. No. 4,072,487 issued to Irwin which shows a cylindrical filter in an open bottomed chamber. Air flow in the Irwin patent is radially inward so that dust collects on the exterior of the cylindrical filter element. Although the Dahl and Irwin patents overcome the problems of accumulated dirt in a filter chamber, these filters are still awkward and messy to clean. Furthermore, drop off from these filters causes additional dust and dirt particles to accumulate on the back window and rearward section of the tractor cab.

Accordingly, it is an objective of this invention to provide a ventilation system having a filter that traps dust and other airborne particulate material and prevents drop off of these particles.

It is a further objective of this invention to provide a filter that is easily and cleanly removed from an air filter chamber.

Other objects and advantages of the present invention will become more apparent to those skilled in the art in view of the following description and the accompanying drawings.

SUMMARY OF THE INVENTION

The present invention relates to a ventilation system for a vehicle cab or the like which takes in fresh air from the outside of the cab, filters the air, and transfers the air to the inside of a cab under forced ventilation. Air is moved from an inlet outside the cab to an outlet within the cab through a passageway containing a filter element. The air filter element has a hollow interior portion into which fresh air is directed and in which dust and particulate material is collected. Air flows out of the filter through sides containing filter material. The passageway is provided with means for removing the filter from the passageway and directing all fresh air through the filter element. Arrangement of the filter and passageway is such that a dust impervious surface is underneath the collected particles during filter removal and operation.

The invention further relates to the use of a tubular shaped filter having an open end for receiving fresh air into the interior of the filter and flow of filtered air out through exterior sides containing a filter material.

The invention also contemplates the addition of heat exchange means downstream of the filter for changing the heat content of the air and means for distributing conditioned air throughout the cab. In a more specific embodiment, air from the interior of the cab is recirculated through the heat exchange means and distributed throughout the cab with conditioned or unconditioned fresh air. It is further comtemplated that the invention use a continuous pressurization blower for supplying air to the filter element and a second stage blower for distributing filtered fresh air and recirculated air throughout the cab.

In yet another embodiment, the system is roof-mounted in a vehicle cab and the cab roof is raised to allow removal and cleaning of the filter.

Various other features of the invention will be apparent from a consideration of the specification, claims and drawings.

DESCRIPTION OF THE PREFERRED EMBODIMENT

Figure 1:
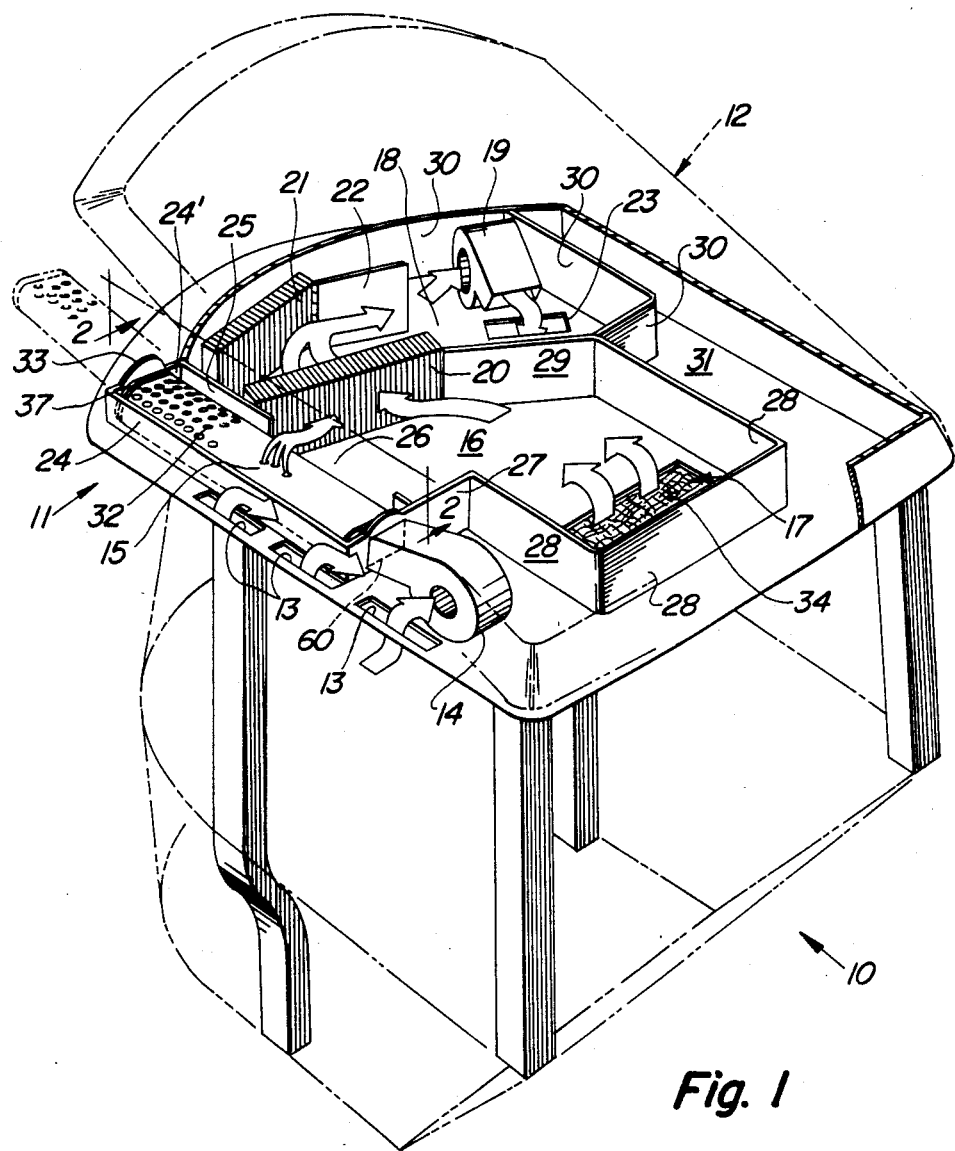
FIG. 1 is a perspective view of a vehicle cab and a ventilation system disposed therein.

Referring first to FIG. 1, a general outline view of a tractor cab with a ventilation system in the roof is shown in perspective. In this view, the cab roof 12 is shown open and cut away to fully reveal the ventilation system 11. Ventilation system 11 also has its top closure plate removed to fully reveal the components of the ventilation system.

Looking first at fresh air flow through the ventilation system, fresh air is drawn in through fresh air inlets 13 by a blower 14 and is pushed into a fresh air filter 15. Filter 15 is located in filter chamber 32. Filtered air exits the outer surface of the filter 15 and enters plenum 16. Plenum 16 also contains a recirculation air inlet 17 which takes air from the interior of the cab. An air filter 34 is placed over recirculation inlet 17 for removing dust and particles from the air within the vehicle cab. This filter has a very light dust loading due to the removal of most particulates from the cab by filter 15. A circulation air blower 19 draws filtered air and recirculated air from plenum 16 into an air conditioning chamber 18. Combined air flow entering air conditioning chamber 18 passes first through an evaporator core 20. Evaporator core 20 provides heat exchange with a cooling medium in a manner well-known to those skilled in the art. An air blend door 22 is shown in open position allowing air passing through the evaporator core 20 to move directly to blower 19. Door 22 is movable to a closed position, wherein the right end of the door is swung against evaporator core 20, causing air to pass through heater core 21 which is used to heat air before entering blower 19. Air blower 19 directs air into the cab through an air exit 23 which is connected to an air distribution system (not shown).

Air filter chamber 32, plenum 16 and air conditioning chamber 18 all have the cab ceiling 31 as a common bottom, and a common top sealing element which has been removed from FIG. 1. Plenum 16 is defined by the sidewalls 27, 28, 29 and evaporator core 20. The air conditioning chamber is defined by the sidewalls 25, 30, 29 and evaporator core 20. The sides of air filter chamber 32 are defined by the sidewalls 25, 24, 24' and 27 with wall 27 having a blower inlet opening 60 for air exiting blower 14. Front wall 24' of the filter chamber has an opening 37 for removal of the air filter. During operation, this opening is closed by a cover 33 which serves as a closure element.

Figure 2:
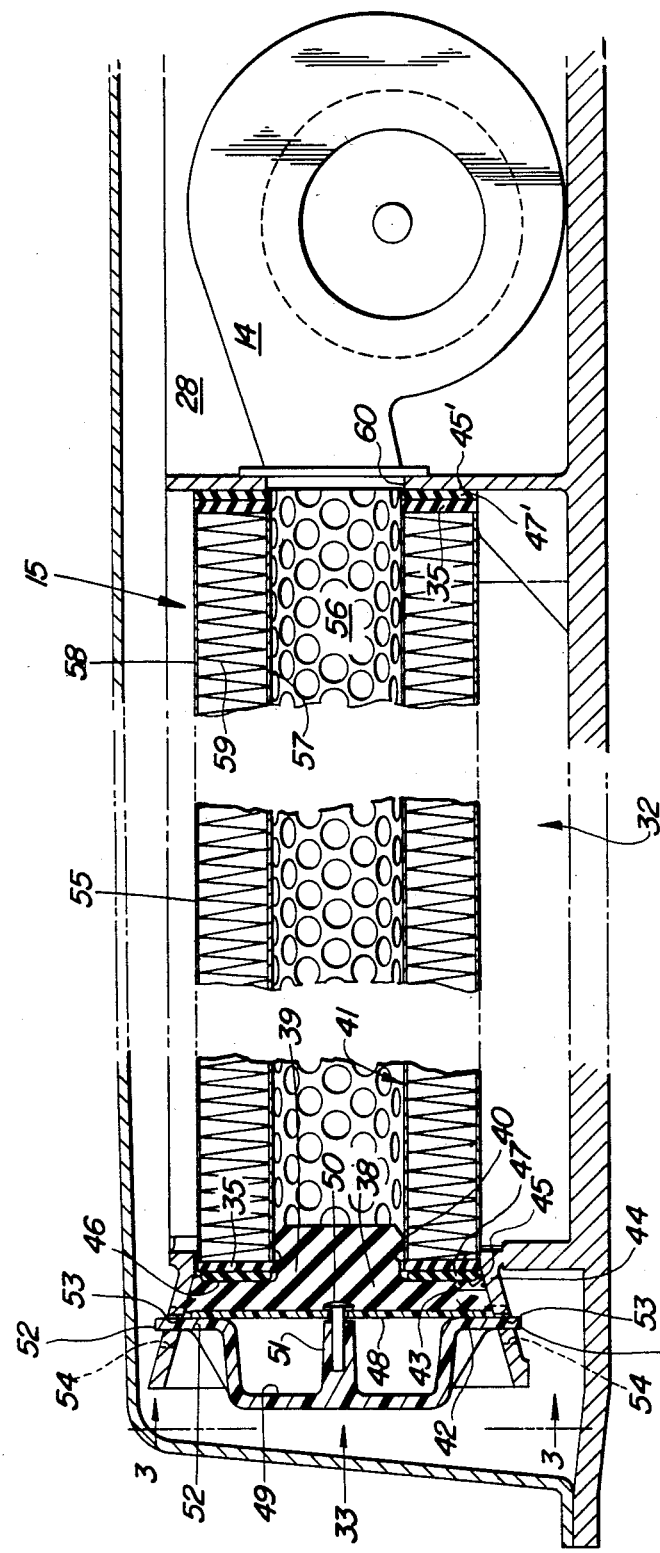
FIG. 2 is a section of the filter chamber and enclosure taken along section 2—2 of FIG. 1.

Filter 15 is shown in more detail in FIG. 2. The air filter is elongate in shape and has an axial cross section generally oval in shape defining an interior collection space 56. In its preferred form, the length of filter 15 exceeds its minimum inside diameter. A center portion 55 of the filter is constructed of an inner and an outer perforated metal retainer 57 and 58, respectively. Retainers 57 and 58 enclose a corrugated paper filter element 59. Filter element 59 traps dirt and particulates within interior space 56 as air flows from the interior of the filter out through the sides. Filter element 59 and retainers 57 and 58 are attached to a sealing band 35 at each end of the filter. Sealing bands 35 are made of a rigid material and are used to seal the interior of the filter at each end. A gasket 47, 47' made of resilient material, in this case foam, is attached to the outer face of each band 35. The gaskets 47, 47' each have an outer contact face 45, 45' contacting the chamber wall 27 or the plug 33. Since both sides of the filter are open, upon removal, the filter is located with its major axis in a horizontal plane so that dirt does not empty into the air filter chamber or on the operator.

FIG. 2 further shows filter 15 within filter chamber 32 with chamber cover 33 closing the chamber opening and the filter end. Chamber cover 33 simultaneously seals the end of filter 15 adjacent the cover 33 and filter chamber opening 37 (see FIG. 1). This simultaneous sealing is provided by a chamber plug 38. Plug 38 has a filter stop 39 and a chamber disc 42 which are used to seal the filter and the chamber opening, respectively. The innermost extending portion of filter plug 38 is filter stop 39. Stop 39 is shaped to match the cross section of inner retainer 57 but is of a slightly larger dimension such that a rib 40 on the stop forms an interference fit with the retainer thereby gripping the filter for removal. Chamber disc 42 has an outer side 43 which contacts a flared neck 44 of the chamber opening. A contact surface 46 of disc 42 pushes against gasket 47 of the filter. Compression of ring 47 provides pressure for sealing the inlet end of filter 15. Force from filter cover 33 also acts on gasket 47' pushing filter end face 45' against wall 27 in a sealing relationship about blower inlet opening 60 which prevents bypassing of incoming air.

Altogether, chamber cover 33 consists of plug 38, a backing plate 48 and a handle 49. Chamber plug 38 is constructed of a resilient rubber material and attached to backing plate 48. Backing plate 48 and handle 49 are made of a rigid material with backing plate 48 secured to a center post 51 of handle 49 by a rivet 50 which is force fit into center post 51. Rivet 50 also allows handle 49 to be rotated with respect to cover plate 48 and plug 38.

Handle 49 transmits sealing force to plug 38 by contact of the end tangs 52, which extend outward from the handle 49, with openings 53 in flared neck 44. Openings 53 also contain ramp portions 54 for increasing the axial force transmitted by the cover plate as the handle is locked into position.

Figure 3:
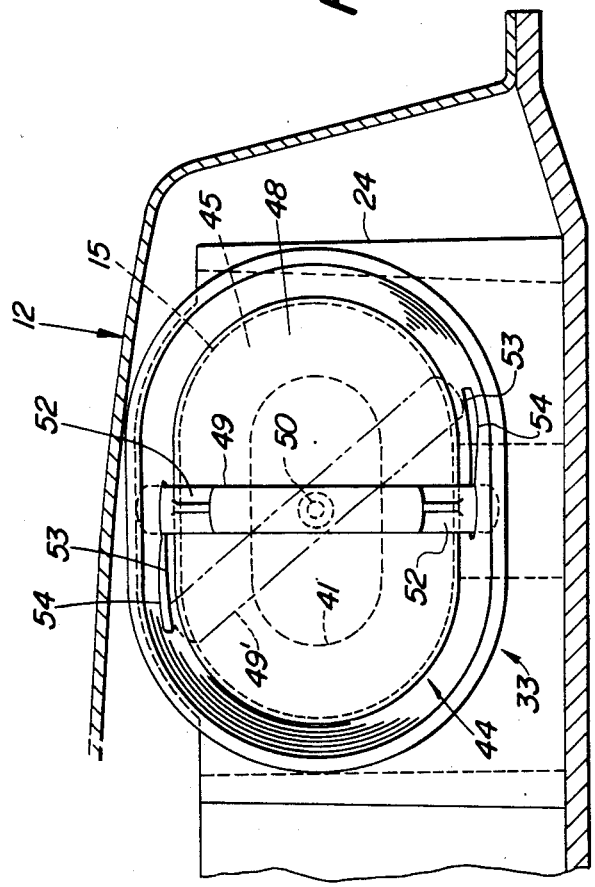
FIG. 3 is an end view of the filter chamber and closure door taken along line 3—3 of FIG. 2.

The locking action of the handle as it contacts openings 53 can be more fully understood by reference to FIG. 3. Located behind the cover and indicated by hidden lines is end surface 45 of the filter. These lines show the oval configuration of the filter element. The position of the handle shown in phantom lines and indicated by 49' corresponds to the cover in an unlocked position. As the handle is rotated clockwise, a tang 52 projects into neck 44 of the chamber opening and through opening 53. As rotation of the handle continues, the outer surface of end tang 52 contacts ramp 54 thereby forcing the handle and plug into contact with the filter element and neck 44. The inward movement of the plug provides sealing pressure to the opposite filter end and is caused by the inward slope of ramp 54 as the handle moves in a clockwise direction.

Operation of the ventilation system and servicing of the filter proceeds in the following manner. Air flows through the ventilation system in the manner described in FIG. 1. Fresh air entering the interior of filter 15 by the force of blower 14 is filtered and then mixed with recirculated air in plenum which is further conditioned and carried to the cab by the action of air blower 19. Particulates removed by filter 15 accumulate on the inside of the filter gradually restricting the air flow area within the filter. After some time, the filter is in need of servicing. In order to service the filter, the operator opens the roof 12 of cab 10 and turns handle 49 of filter cover 33. When rotated counterclockwise, cover 33 is unlocked and removed from the neck opening 44. Filter 15 is then slid out horizontally through neck opening 44, as shown in FIG. 1, and serviced by removing dirt therefrom. In the horizontal position, accumulated dust remains in the filter as the filter is removed. After cleaning, the filter is slid back into filter chamber 32 and cover 33 is replaced in nozzle neck 44. The handle of cover 33 is then rotated clockwise to provide sealing pressure to the inlet end of filter 15 and to push disc side 43 in sealing contact with nozzle neck 44 while filter stop 39 is pushed into contact with inner surface 41 of the filter in an interference fit.

Although this invention has been described by reference to a preferred embodiment, those skilled in the art can appreciate numerous modifications, adaptations and variations of this invention. Thus the scope of this invention is only to be limited by the appended claims.

We claim:

1. A ventilation system for a vehicle cab or the like having, an air inlet exterior to the cab, and an air outlet inside said cab for delivering air to the interior of said cab, said system comprising an air flow passageway connecting said air inlet to said air outlet, said passageway having a first contact surface about the inside of said passageway; means for moving air through said passageway from said air inlet to said air outlet; a tubular air filter for collecting and confining airborne particulates located within said passageway and having a hollow interior for collecting and confining airborne particulates, said filter having an axial length greater than at least one inner diameter dimension, a filter inlet at one end in communication with said hollow interior, a second contact surface surrounding said filter inlet, and at least one side containing a filter material impermeable to airborne particulates; means, external to the interior of said filter, for pressing said contact surfaces together in a sealing relationship and securing said filter in said passageway with its longitudinal axis in a horizontal plane and a diameter dimension less than the axial length of the filter in a vertical plane when said cab is level; and means for removing said filter from said passageway such that a side of said filter remains under collected particulates during filter removal.

2. The ventilation system of claim 1 wherein said filter is open at both ends and the end opposite said inlet end is blocked by a closure element, said closure element supplying said means for pressing said contact surfaces together.

3. The ventilation system of claim 2 wherein said air moving means is upstream of said filter.

4. The ventilation system of claim 3 wherein said filter is oval in cross section and its minor diameter lies in a vertical plane when the filter is secured in said passageway.

5. The device of claim 1 wherein said means for removing said filter comprises a filter removal opening defined by said passageway said opening and having a location along the longitudinal axis of said filter, and a cover is provided to seal said filter removal opening, said cover having a pivotably mounted latch thereon for engaging a set of fixed ramps, engagement of said latch and ramps providing, in part, said means for pressing said contact surfaces together.

6. An air conditioning device for a vehicle cab or the like having an air inlet open to the exterior of the cab, an air outlet open to the interior of the cab; an air passageway for directing air from said air inlet to the air outlet, said passageway including an air filter chamber having a filter chamber inlet opening in communication with said air inlet and a filter chamber outlet opening, a first contact surface surrounding said filter chamber inlet opening, and an air conditioning chamber having a conditioning chamber inlet in communication with the filter chamber outlet opening and a conditioning chamber outlet in communication with said air outlet; means in said passageway for moving air from said air inlet through said chambers and delivering pressurized air to said air outlet, said air movement means discharging air directly into said filter chamber opening; an air filter, for collecting and confining airborne particulates, located within said filter chamber, said filter having a tubular shape, a hollow interior when in said filter chamber, an axial length greater than its minimum diameter, a filter inlet opening at one end surrounded by a second contact surface, and filter material about its sides, said filter material being impervious to airborne particulates; means for maintaining the longitudinal axis of said filter in a horizontal plane and said minimim diameter in a vertical plane when said cab is level; a filter removal opening defined by said filter chamber and located along the longitudinal axis of said filter for removing said filter from said filter chamber; and means, external to the interior of said filter, for closing said filter removal opening and pressing said first and second contact surfaces together in a sealing relationship.

7. The device of claim 6 wherein said means for closing said filter removal opening comprises a cover plate, said cover plate sealingly surrounding the periphery of said filter removal opening, and a latch pivotally mounted on said cover plate and engaging a set of ramps, fixed with respect to said filter chamber, to sealingly urge said cover plate against the periphery of said filter removal opening and to provide, in part, said means for pressing said contact surfaces together.

8. The device of claim 7 wherein said filter is open at both ends with the end opposite said filter inlet being closed by said cover plate.

9. The device of claim 8 wherein said cover plate has a plug for sealing and engaging one of said filter ends and a disc for sealing said filter removal opening.

10. The device of claim 9 wherein said device is located immediately below the roof of said cab.

11. The device of claim 10 wherein said cab has a raiseable roof which provides access to the filter removal opening.

* * * * *